United States Patent
Goodrich

(10) Patent No.: US 8,078,334 B2
(45) Date of Patent: Dec. 13, 2011

(54) UNOBTRUSIVE SYSTEM AND METHOD FOR MONITORING THE PHYSIOLOGICAL CONDITION OF A TARGET USER OF A VEHICLE

(76) Inventor: Alan Goodrich, Marblehead, MA (US)

( * ) Notice: Subject to any disclaimer, the term of this patent is extended or adjusted under 35 U.S.C. 154(b) by 988 days.

(21) Appl. No.: 12/009,857

(22) Filed: Jan. 23, 2008

(65) Prior Publication Data

US 2008/0183388 A1    Jul. 31, 2008

Related U.S. Application Data

(60) Provisional application No. 60/881,959, filed on Jan. 23, 2007.

(51) Int. Cl.
  *G05D 1/02*    (2006.01)
(52) U.S. Cl. ............... 700/300; 188/1.11 R; 188/1.11 L; 348/143; 348/158; 2/159; 2/456; 2/463; 340/454; 340/576; 340/905; 119/771
(58) Field of Classification Search ............... 701/300; 188/1.11 R, 1.11 L; 348/143, 158; 2/159, 2/456, 463; 340/454, 576, 905; 119/771; 446/430; 362/103, 180; 473/332, 342, 329
  See application file for complete search history.

(56) References Cited

U.S. PATENT DOCUMENTS

| | | | |
|---|---|---|---|
| 4,909,260 A | 3/1990 | Salem et al. | |
| 5,499,182 A | 3/1996 | Ousborne | |
| 5,574,641 A | 11/1996 | Kawakami et al. | |
| 5,645,607 A * | 7/1997 | Hickey | 623/23.35 |
| 5,729,619 A | 3/1998 | Puma | |
| 5,805,079 A | 9/1998 | Lemelson | |
| 5,829,782 A | 11/1998 | Breed et al. | |
| 5,846,206 A | 12/1998 | Bader | |
| 5,942,979 A | 8/1999 | Luppino | |
| 6,060,989 A * | 5/2000 | Gehlot | 340/576 |
| 6,104,296 A | 8/2000 | Yasushi et al. | |
| 6,225,890 B1 | 5/2001 | Murphy | |
| 6,254,127 B1 | 7/2001 | Breed et al. | |
| 6,293,361 B1 | 9/2001 | Mueller | |
| 6,313,749 B1 | 11/2001 | Horne et al. | |
| 6,353,396 B1 | 3/2002 | Atlas | |
| 6,545,607 B2 | 4/2003 | Bredow et al. | |
| 6,631,989 B2 | 10/2003 | Odom et al. | |
| 6,734,799 B2 | 5/2004 | Munch | |
| 6,756,903 B2 | 6/2004 | Omry et al. | |

(Continued)

FOREIGN PATENT DOCUMENTS

WO    WO 99/32317    7/1999

*Primary Examiner* — James Trammell
*Assistant Examiner* — McDieunel Marc
(74) *Attorney, Agent, or Firm* — Iandiorio Teska & Coleman

(57) ABSTRACT

An unobtrusive system for monitoring the physiological condition of a target user of a vehicle including a wearable device affixed to the target user. A measurement subsystem is releasably coupled to the wearable device configured to measure a concentration of at least one analyte in the blood of the target user at one or more time increments. A proximity sensor is configured to detect the location of the wearable device. A vehicle control subsystem is responsive to the proximity sensor and the measurement subsystem and is configured to determine if the wearable device is proximate a predetermined location in the vehicle and configured to determine if the measured concentration of the at least one analyte exceeds a predetermined threshold concentration level, and based on such a determination, initiate one or more predetermined actions.

34 Claims, 6 Drawing Sheets

U.S. PATENT DOCUMENTS

| | | |
|---|---|---|
| 7,279,132 B2 * | 10/2007 | Sultan et al. .................... 422/83 |
| 7,700,305 B2 * | 4/2010 | Toranto et al. ............... 435/7.21 |
| 2002/0128769 A1 | 9/2002 | Der Ghazarian et al. |
| 2003/0011481 A1 | 1/2003 | Bjorkman |
| 2003/0065253 A1 | 4/2003 | Stivoric et al. |
| 2004/0044293 A1 | 3/2004 | Burton |
| 2004/0083031 A1 * | 4/2004 | Okezie .............................. 701/1 |
| 2004/0085187 A1 | 5/2004 | Gotfried et al. |
| 2004/0097797 A1 | 5/2004 | Porges et al. |
| 2004/0145496 A1 | 7/2004 | Ellis |
| 2004/0152957 A1 | 8/2004 | Stivoric et al. |
| 2004/0253657 A1 | 12/2004 | Ullman et al. |
| 2006/0006990 A1 | 1/2006 | Obradovich |
| 2006/0182661 A1 * | 8/2006 | Aquila ........................... 422/84 |
| 2007/0077176 A1 * | 4/2007 | Lambert et al. ............ 422/82.05 |

* cited by examiner

UNOBTRUSIVE SYSTEM AND METHOD FOR MONITORING THE PHYSIOLOGICAL CONDITION OF A TARGET USER OF A VEHICLE

RELATED APPLICATIONS

This application claims benefit of and priority to U.S. Provisional Patent Application No. 60/881,959 filed Jan. 23, 2007, incorporated by reference herein.

FIELD OF THE INVENTION

This invention relates to an unobtrusive system and method for monitoring the physiological condition of a target user of a vehicle.

BACKGROUND OF THE INVENTION

One in three drivers in the United States will likely be involved in an alcohol related vehicle accident. Although the penalty for driving under the influence may include the loss of driving privileges and/or jail time, about 65% of those convicted from driving while intoxicated (DWI) continue to drive vehicles while intoxicated and become habitual offenders. Current penalties for DWI do little to deter such habitual offenders.

The use of both legal and illegal drugs has also been linked to numerous vehicle accidents. Most recently pharmaceutical sleep aids (e.g., Ambien®) has been linked to several high profile driving accidents. However, many of these incidents go undetected due to a lack of in-field testing systems. It has been estimated that about 329,000 incidents occur each year in the United States where the operator of the vehicle has been arrested for drug possession.

Millions of vehicle operators suffer from health related conditions that may prevent their ability to safely operate a vehicle, e.g., epilepsy, heart disease, diabetes, and the like. Similar to drug related incidents, there are currently no in-field testing systems to determine if a vehicle accident has been caused due to a health related condition of the operator.

Many conventional systems and methods for testing blood alcohol level of a driver of a vehicle are obtrusive to the user, require cooperation from the user, are easily subverted, often produce false positive tests, must be installed in the vehicle of the DWI offender, do not target the DWI offenders, are expensive, and typically ineffective at preventing habitual offenses.

For example, a conventional breathalyzer based system requires the DWI offender to first blow into the breathalyzer to start the vehicle. Then, at random time intervals, the system emits a signal which requires the offender to perform another test. This process requires the user, while driving the vehicle, to reach over and grab the breathalyzer to perform the test. As can be seen, such a process is obtrusive, requires cooperation of the user, and is possibly dangerous to the DWI offender driving the vehicle, much the same way that cell phone use is a distraction to drivers. The system can also be easily subverted by allowing a sober passenger in the vehicle to take the test. Such systems and methods are also prone to false positive tests, e.g., when the offender has used an alcohol based mouthwash, cough syrup, or prescription sprays. Additionally, the breathalyzer must be installed in the vehicle of the DWI offender. Thus, such a design does not target the DWI offender and is offensive and obtrusive to other users of the vehicle who must utilize the breathalyzer to drive the vehicle. Conventional breathalyzer-based systems also provide no means to test whether the driver of a vehicle is under the influence of illegal or abused prescription drugs or has a health related condition that prevents the driver from safely operating the vehicle.

BRIEF SUMMARY OF THE INVENTION

It is therefore an object of this invention to provide an unobtrusive system and method for monitoring the physiological condition of a target user of a vehicle.

It is a further object of this invention to provide such a system and method which can measure the level of one or more analytes in the blood of the target user while the vehicle is in operation.

It is a further object of this invention to provide such a system and method which can measure the level of blood alcohol level of the target user while the vehicle is in operation.

It is a further object of this invention to provide such a system and method which can measure the level of one or more analytes related to health related conditions that may prevent the ability of a target user to safely operate a vehicle.

It is a further object of this invention to provide such a system and method which requires no cooperation from the user to test of the level of one or more analytes in the blood of the target user.

It is a further object of this invention to provide such a system and method which is less dangerous.

It is a further object of this invention to provide such a system and method which is not easily subverted.

It is a further object of this invention to provide such a system and method which significantly reduces the occurrence of false positive tests.

It is a further object of this invention to provide such a system and method which is more accurate.

It is a further object of this invention to provide such a system and method which detects changes in a target offenders' condition during vehicle operation.

It is a further object of this invention to provide such a system and method which increases the likelihood offenders will be detected and apprehended.

It is a further object of this invention to provide such a system and method which targets a DWI offender.

It is a further object of this invention to provide such a system and method which is unobtrusive and non-offensive to non-DWI offenders.

It is a further object of this invention to provide such a system and method which is less expensive.

It is a further object of this invention to provide such a system and method which helps prevent habitual DWI offenses.

It is a further object of this invention to provide such a system and method which safely increases the driving privileges of persons commonly issued medical conditional licenses, or who are restricted from operating motor vehicles.

The subject invention, however, in other embodiments, need not achieve all these objectives and the claims hereof should not be limited to structures or methods capable of achieving these objectives.

This invention features an unobtrusive system for monitoring the physiological condition of a target user of a vehicle including a wearable device affixed to the target user. A measurement subsystem is releasably coupled to the wearable device and is configured to measure a concentration of at least one analyte in the blood of the target user at one or more time increments. A proximity sensor is configured to detect the location of the wearable device. A vehicle control subsystem is responsive to the proximity sensor and the measurement subsystem and is configured to determine if the wearable device is proximate a predetermined location in the vehicle and configured to determine if the measured concentration of the at least one analyte exceeds a predetermined threshold concentration level, and based on such a determination, initiate one or more predetermined actions.

In one embodiment, the at least one analyte may include an analyte chosen from the group consisting of: alcohol, drugs, glucose, proteins, enzymes, hormones, glucose ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, narcotics, tetrahydrocannabinol, cytochrome, various proteins and chromophores, microcalcifications, electrolytes, sodium, potassium, chloride, bicarbonate, and hormones. The measurement subsystem may be configured as an infrared spectrometer. The infrared spectrometer may include one or more processors and a power supply located in the measurement subsystem and one or more processors, a light source, and a photodetector located in the wearable device. The light source may emit light at a predetermined wavelength into the subcutaneous layer of the skin of the target user and the photodetector detects the wavelength of the reflected light emitted the subcutaneous layer of the skin of the target user. The measurement subsystem may determine a change in the wavelength of the light emitted by the light source and the light detected by the photodetector to determine the concentration of the at least one analyte in the blood of the target user. The measurement subsystem may be uniquely matched to the wearable device. The measurement subsystem may include a unique RF ID tag. The wearable device may include a unique RF ID tag. The measurement subsystem may be configured to transmit physiological data of the measured concentration of the at least one analyte in the blood of the target user to the vehicle control subsystem when the RF ID tag of the measurement subsystem uniquely matches the RF ID tag of the wearable device. The wearable device may include a processor configured to determine the identity of the RF ID tag of the wearable device. The measurement subsystem may include a processor configured to determine if the identity of RF ID tag located in the measurement subsystem and if the RF ID tag of the measurement subsystem uniquely matches the RF ID tag of the wearable device. The vehicle control subsystem may include one or more processors, one or more transmitters and one or more receivers. The system may further include a power supply coupled to the vehicle control system. The wearable device may include one or more processors and one or more transmitters. The wearable device may include a tamper proof bracelet. The wearable device may include a tamper proof anklet. The wearable device may be coupled to the measurement subsystem by one or more electrical contacts. The measurement subsystem may include one or more contacts for connecting to a power source for recharging the power supply. The system may further include one or more gaskets disposed between the measurement subsystem and the wearable device configured to adjust the distance between the measurement subsystem and the wearable device and minimize extraneous light. The proximity sensor may include a DC pulse magnetic resonator configured to detect the distance and spatial orientation of a magnetic sensor located in the wearable device. The proximity sensor may be located in the vehicle. The proximity sensor may be located proximate the steering column of the vehicle. The proximity sensor may define the predetermined location in the vehicle. The vehicle control system may be configured to determine if the wearable device is proximate the predetermined location in the vehicle. The predetermined location may be the area proximate the driver's area of the vehicle. The proximity sensor may communicate to the vehicle control subsystem by a direct connection. The proximity sensor may communicate to the vehicle control system wirelessly. The one or more time increments may include a first time the target user starts the vehicle and thereafter at random and/or predetermined time increments. The one or more predetermined actions may include an action chosen from the group consisting of: not allowing the vehicle to start, speed governing of the vehicle, a global positioning system response to law enforcement personnel as to the location of the vehicle, emitting light from the vehicle, and sound from the vehicle. The predetermined threshold concentration level may include about 0.08% in the blood of the target user and/or a measurable amount of illegal drugs in the blood of the target user and/or a change in protein-c levels that may be indicative of a heart attack in the blood of the target user and/or an unsafe blood glucose level in the blood of the target user.

This invention also features an unobtrusive method for monitoring the physiological condition of a target user of a vehicle including affixing a wearable device to a target user, measuring the concentration of at least one analyte in the blood of a target user in the vehicle one or more time increments, determining if the wearable device is proximate a predetermined location in the vehicle, and determining if the measured concentration of at least one analyte exceeds a predetermined threshold concentration level and based on such a determination, initiate one or more predetermined actions.

In one embodiment, the at least one analyte may include an analyte chosen from the group consisting of: alcohol, drugs, glucose, proteins, enzymes, hormones, glucose ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, narcotics, tetrahydrocannabinol, cytochrome, various proteins and chromophores, microcalcifications, electrolytes, sodium, potassium, chloride, bicarbonate, and hormones. The method may further include the step of emitting light at a predetermined wavelength into the subcutaneous layer of the skin of a target user and detecting the wavelength of the light emitted from the subcutaneous layer of the skin of the target user. The method may further include the step of determining a change in the wavelength of the light emitted into the subcutaneous layer of the skin of the target user, and the light emitted out of the subcutaneous layer of the skin of the target user to determine the concentration of the at least one analyte in the blood of the target user. The method may further include the step of determining if the wearable device is uniquely matched to the measurement subsystem. The one or more actions may include an action chosen from the group consisting of: not allowing the vehicle to start, speed governing of the vehicle, a global positioning system response to law enforcement personnel as to the location of the vehicle, emitting of light from the vehicle, and emitting sound from the vehicle. The predetermined threshold concentration level may include about 0.08% alcohol in the blood of the target user, and/or a measurable amount of illegal drugs in the blood of the target user and/or a change in protein-c levels that may be indicative of a heart attack in the blood of the target user and/or an unsafe blood glucose level in the blood of the target user.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
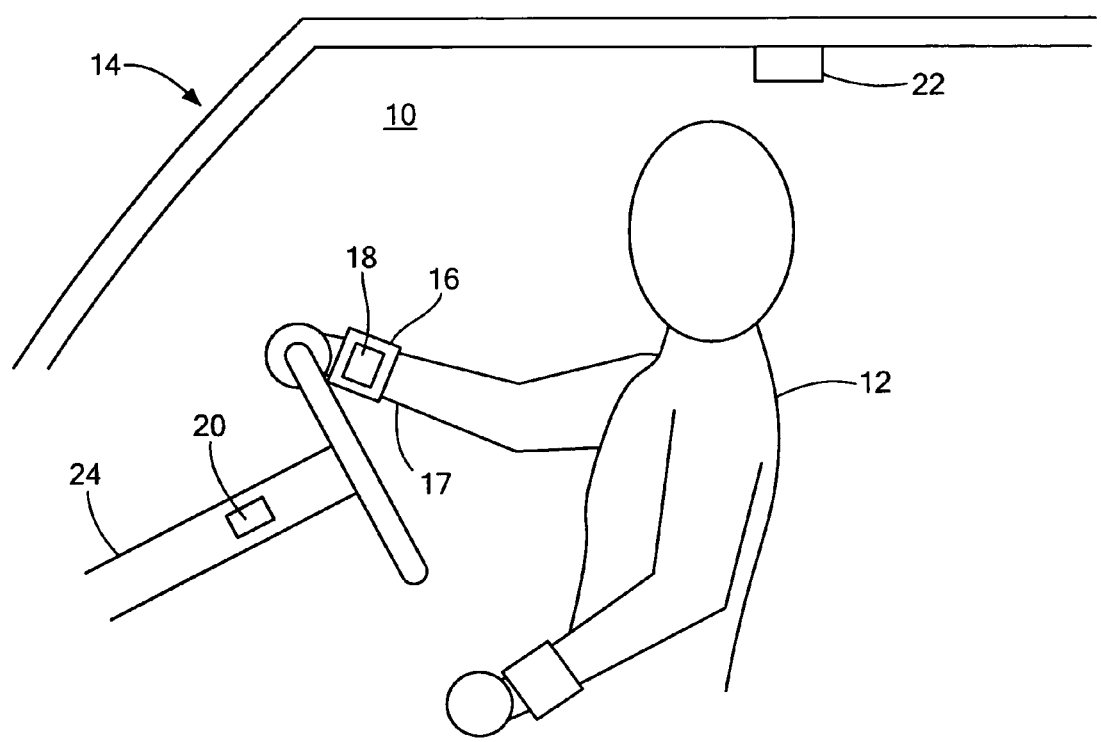
FIG. 1 is a schematic side-view showing one embodiment of the primary components of the unobtrusive system for monitoring the physiological condition of a target user of a vehicle of this invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

There is shown in FIG. 1 one embodiment of unobtrusive system 10 for monitoring the physiological condition of target user 12 of vehicle 14. System 10 includes wearable device 16 affixed to target user 12, e.g., a DWI offender. In one example, wearable device 16 may be tamperproof bracelet attached about wrist 17 of target user 12. In other designs, wearable device 16 may be an anklet (not shown) worn about the leg of target user 12. Wearable device 16 may be designed in such a way that when it has been tampered with it can easily be detected by law enforcement personnel. Further details regarding the design of wearable device 16 are disclosed in U.S. Pat. No. 5,959,533, incorporated by reference herein.

Measurement subsystem 18 is releasably coupled to wearable device 16 and measures the concentration of at least one analyte in the blood of target user 12 at one or more time increments, e.g., when the vehicle ignition is first engaged and thereafter at random time increments. In one embodiment, the measurement subsystem 18 quantifies the concentration of a particular analyte concentration in the blood of target user 12 at vehicle ignition and randomly, e.g. at least once every 10 minutes, during vehicle operation, unbeknown to the vehicle operator.

In one embodiment, measurement subsystem 18 may be configured as an infrared spectrometer (discussed in further detail below) and unobtrusively and accurately measures the concentration of one or more analytes in the blood of target user 12, which may include, inter alia, blood alcohol, drugs, glucose, proteins, enzymes, hormones, glucose, ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, narcotics, tetrahydrocannabinol, cytochrome, various proteins and chromophores, microcalcifications, electrolytes, sodium, potassium, chloride, bicarbonate, hormones, and the like. See e.g., U.S. Pat. No. 7,271,912, incorporated by reference herein.

Measurement subsystem 18 is typically calibrated for a particular target user 12 to detect the concentration of any one or more of the aforementioned analytes, e.g., a blood level alcohol level exceeding about 0.08% (one example of a legally defined limit to safely operate a vehicle), a change in protein-c levels that may be indicative of a likely heart attack, or a change in blood glucose level that may indicate an unsafe condition. Calibration of measurement subsystem 18 is performed at the time system 10 is installed in vehicle 14 and provides a means of relating light absorption data detected by measurement subsystem 18 (e.g., a spectrometer, discussed below) to one or more physiological conditions, e.g., the concentration of one or more analytes in the blood of target user 12. Thus, system 10 can measure the blood alcohol level in the blood of target user, as well as the level of one or more drugs, glucose, or other analytes that may impair the ability of target user to operate vehicle 14.

Figure 2A:
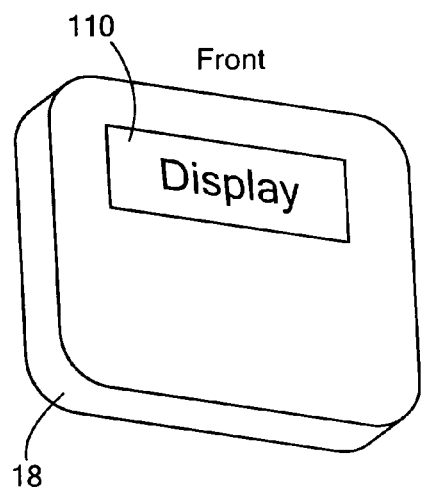
FIGS. 2A-2C are three-dimensional views of one embodiment of the wearable device and measurement subsystem shown in FIG. 1.
Figure 2B:
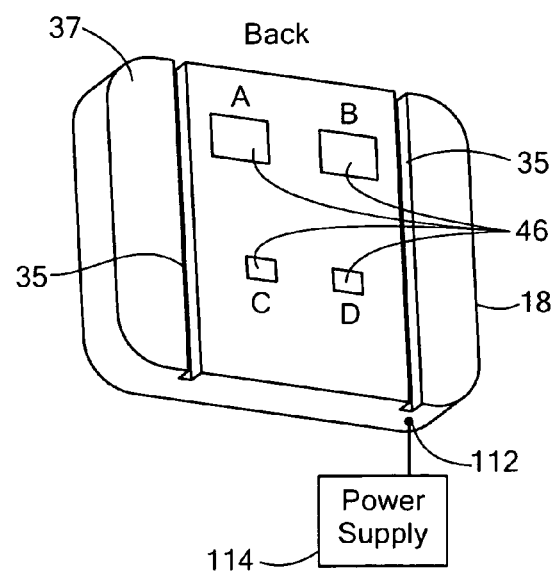
Figure 2C:
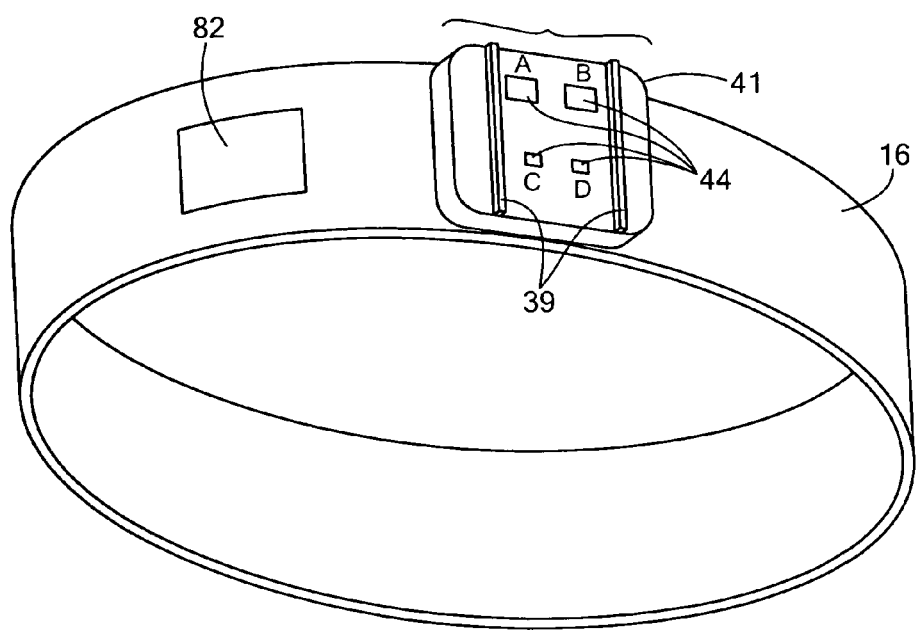

Measurement subsystem 18, FIGS. 2A and 2B, where like parts have been given like numbers, preferably include fasteners 35, FIG. 2B on back 37 of measurement subsystem 18 which releasably engage fasteners 39, FIG. 2C on wearable device assembly 41 attached to wearable device 16. In one design, measurement subsystem 18, FIG. 2B may include contacts 46 which are placed adjacent to contacts 44 on wearable device 16, FIG. 2C, as shown in greater detail in FIG. 3. Contacts 44 and 46 provide the necessary electrical interconnection between measurement subsystem 18 and wearable device 16 which allow measurement subsystem 18. Measurement subsystem 18, FIG. 2B, also includes contact 112 for connecting to remote power supply 114. The result is measurement subsystem 18 can be easily detached from wearable device 16 as needed, e.g., when target user 12 may be exposed to water, e.g., when taking a shower, swimming, and the like, or for charging the power supply of wearable device 16.

Proximity sensor 20, FIG. 1 detects the location of wearable device 16 in vehicle 14. In one design, proximity sensor 20 is located on steering column 24 of vehicle 12. In other designs, proximity sensor 20 may be located under the driver's seat or in a known measurable position in vehicle 14. Proximity sensor 20 is activated by vehicle control subsystem 22 when target user 12 first engages the ignition and thereafter at random time intervals during operation of vehicle 14. In one example, processor $\mu P_4$-70, FIG. 3, where like parts have been given like number, processes signals from proximity sensor 20 by lines 66 and 68 to determine the location of wearable device 16 in vehicle 14. Proximity sensor 20 may also communicate wirelessly to proximity sensor 20. In one design, power supply 101, e.g., a car battery, supplies power to vehicle control subsystem 22.

Figure 3:
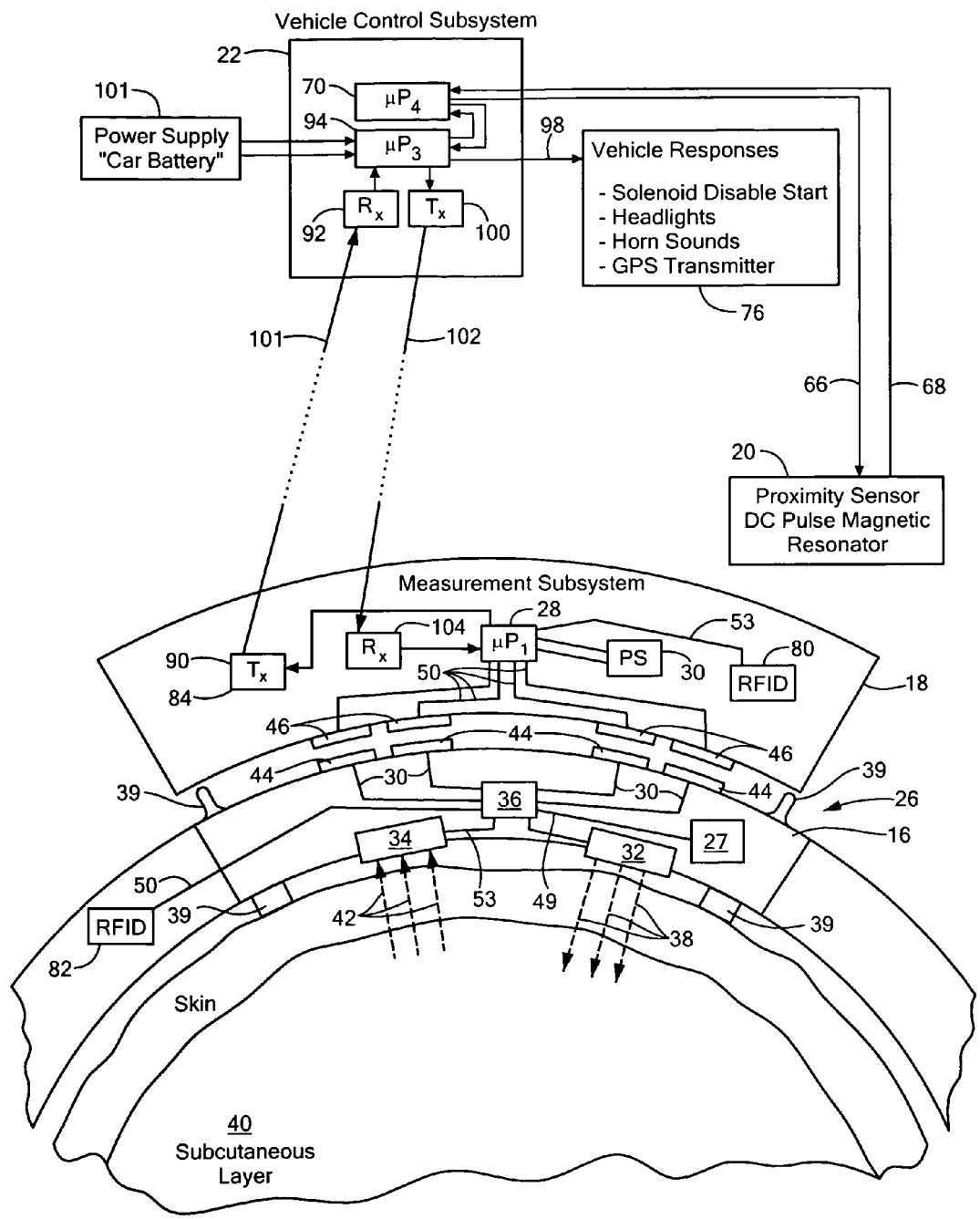
FIG. 3 is a schematic block diagram showing in further detail the primary components of the system shown in FIGS. 1 and 2.
Figure 4:
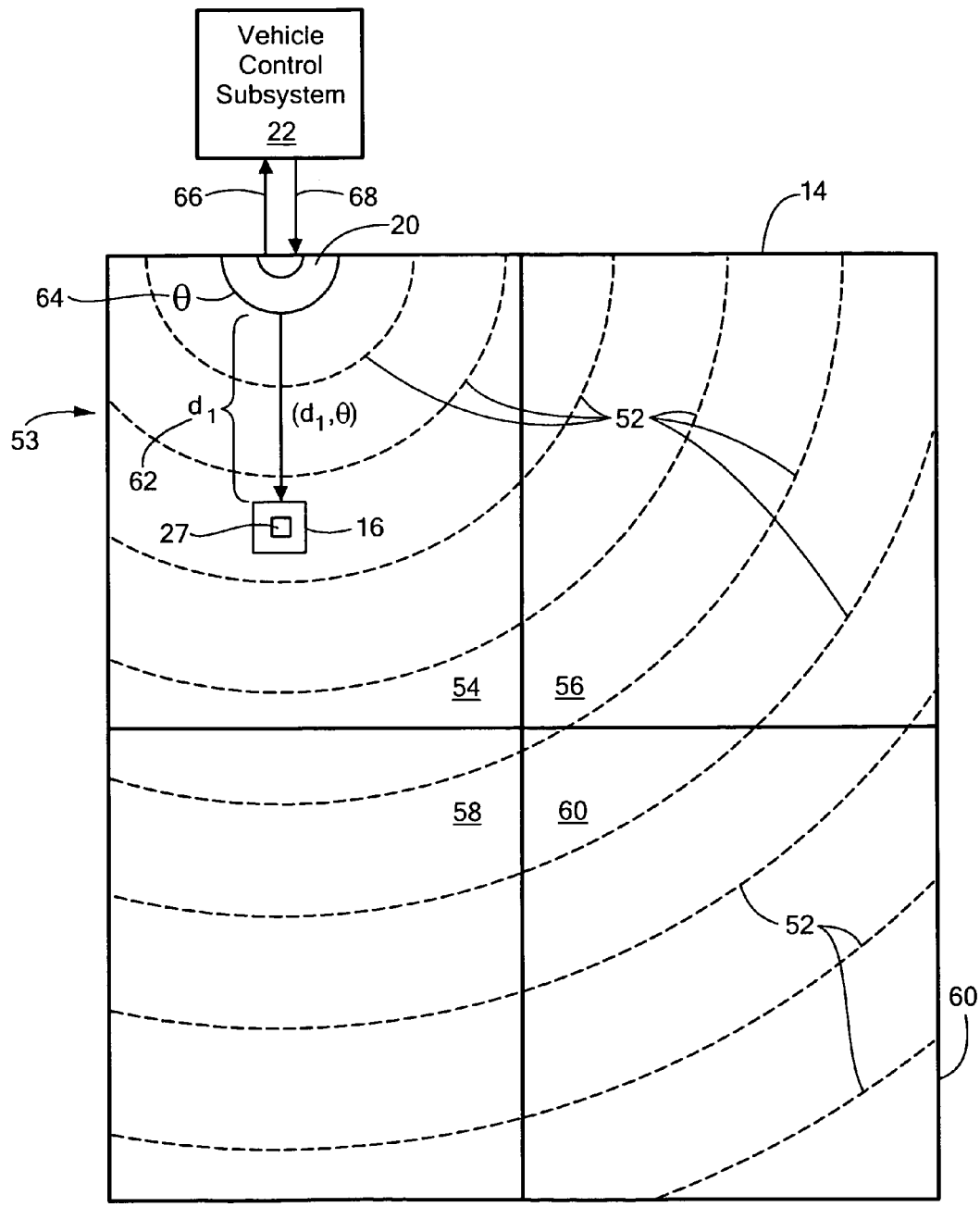
FIG. 4 is a schematic top diagram showing one example of the various zones of a vehicle and an exemplary operation of the proximity sensor shown in FIGS. 1-3.

FIG. 4, where like parts have been given like numbers, shows one example of driver zone 54 and passenger zones 56, 58, and 60 of vehicle 14. In this example, proximity sensor 20 is shown located proximate the front area 53 of driver zone 54, e.g., on the steering column as discussed above. In one embodiment, proximity sensor 20 may be a DC pulse magnetic resonator which emits a series of DC fields 52 which are unaffected by hand or non-metallic objects in its transmission path. One example of one such DC magnetic pulse resonator is a MotionStar® tracker system available from Ascension Technology (Milton, Vt. 05468). Wearable device 16, FIG. 3, includes at least one magnetic sensor 27 which sends binary data by lines 49, 50, 53 and contacts 44, 46 to processor $\mu P_1$-28 which disclose the identity and orientation (e.g., the vector comprised of distance $d_1$-62, FIG. 4 and angle θ-64) of magnetic sensor 27 in wearable device 16. In one example, proximity sensor 20 sends DC fields 52 up to 144 times per second to achieve position accuracy up to 0.3 inches/0.5 degree at a five-foot range. The information about the distance and orientation of magnetic sensor 27 processed by processor $\mu P_1$-28, FIG. 3, is then sent to processor $\mu P_3$-94 in vehicle control subsystem 22, e.g., using transmitter 90 and receiver 92. Processor $\mu_3$-94 of vehicle control subsystem 22 interprets the binary data to determine the location of wearable device 16 in vehicle 14, FIG. 4. In one example, processor $\mu P_3$-94 computes if wearable device 16 affixed to target user 12 is within a vehicle-specific (predetermined) range and at a specified orientation (angle) in driver zone 54, FIG. 4, from vehicle control subsystem 22 to determine if wearable device 16 is in driver zone 54. If wearable device 16 affixed to target user 12 is located at such a predetermined location in driver zone 54, vehicle control subsystem 22 activates measurement subsystem 18, FIGS. 1-3 to measures the concentration of at least one analyte in the blood of target user 12. Further details of proximity sensor 20, e.g., a DC pulse magnetic resonator, are disclosed in the article "Ascension Technology Puts Spotlight on DC Field Magnetic Motion Tracking" by Nancy Anisfield, HP Chronicle, Vol. 17, No. 9, August 2000, incorporated by reference herein.

However before a measurement is taken, vehicle control subsystem 22, FIGS. 1 and 3, preferably determines if measurement subsystem 18 is uniquely matched to wearable device 16. In order to this, measurement subsystem 18, FIG. 3, preferably includes unique RF ID tag 80 and wearable device 16 preferably includes unique RF ID tag 82 (also shown in further detail in FIG. 2C). RF ID tags 80 and 82 communicate to processor $\mu P_3$-28, e.g., using lines 50, 53, and contacts 44 and 46. Processor $\mu P_3$-28 utilizes an algorithm to determine if RF ID tag 80 in measurement subsystem 18 uniquely matches RF ID tag 82 in wearable device 16. When this occurs, measurement subsystem sends signals, indicated 101, to receiver 92 in vehicle control subsystem 22. Further details of the use and construction of RF ID tags 80 and 82 are disclosed in U.S. Pat. Nos. 6,750,769 and 6,717, 516, both incorporated by reference herein. Uniquely matching measurement subsystem 18 to wearable device 16 prevents measurement subsystem 18 which may be calibrated differently, e.g., for a different analyte or user, from being used with wearable device 16 which is attached to the target user 12. If measurement subsystem 18 does not uniquely match wearable device 16, vehicle control subsystem 22 will disable or prevent operation of vehicle 14, FIG. 1. If wearable device 16 is not detected in driver zone 54, FIG. 4, by vehicle control subsystem 22 as discussed above, vehicle control subsystem 22 allows the vehicle 14 to operate or continue to operate normally. When wearable device 16 uniquely matches measurement subsystem 18, vehicle control subsystem 22, FIG. 3 activates measurement subsystem 18, e.g., by sending signals indicated at 102 via transmitter 100 to receiver 102 in measurement subsystem 18 to measure the concentration of at least one analyte in the blood of target user 12.

The result is system 10 is only utilized when a determination is made by vehicle control subsystem 22 that at least one wearable device 16 is located in the driver's area of the vehicle. If no such determination is made, other drivers of vehicle 14 can freely operate vehicle 14. Thus, system 10 effectively targets a user that is required to wear wearable device 16, e.g., a DWI offender, and is unobtrusive and non offensive to other drivers of the vehicle 14

Once vehicle control subsystem 22 has activated measurement subsystem 18 to measures the concentration of at least one analyte in the blood of target user 12, measurement subsystem 18 preferably uses transmitter 90 to send the measured physiological data as signals, indicated at 101, to receiver 92 in vehicle control subsystem 22. Processor $\mu P_3$-94 then uses one or more algorithms to determine if the measured concentration of the analyte in the blood of target user 12 measured by measurement subsystem 18, e.g., the blood alcohol level exceeds a predetermined threshold concentration level. When that condition occurs, vehicle control subsystem 22 initiates one or more predetermined actions 76 based on that determination, e.g., disabling the solenoid of the starter, speed governing of the vehicle, emitting sequences of light, e.g., from the lights of the vehicle, emitting sounds, such as beeping of the horn of the vehicle, or a utilizing a global positioning transmitter to send signals to law enforcement personnel as to location of vehicle 14. Further details regarding the one or more predetermined actions initiated by vehicle control subsystem 22 are disclosed in U.S. Pat. Nos. 6,229,908 and 7,137,471, both incorporated by reference herein.

In one embodiment, measurement subsystem 18, FIG. 3, where like parts have been given like numbers, is configured as infrared spectrometer 26 which measures the concentration of the at least one analyte in the blood of target user 12. Infrared spectrometer 26 typically includes processor $\mu P_1$-28 and power supply 30 located in measurement subsystem 18 and light source 32, e.g., a LED or similar type device, and photodetector 34, e.g., a photodiode, located in wearable device 16. Light source 32 emits light 38 into subcutaneous layer 40 of the skin of target user 12. Photodetector 34 detects the light 42 reflected back from subcutaneous layer of skin 40 and provides electrical signals to processor $\mu P_1$-28. Processor $\mu P_1$-28 determines the change in the wavelength of the light emitted by light source 32 and the light detected by photodetector 34 to measure the amount of light absorbed in subcutaneous layer of skin 40 and determine concentration of at least one analyte in the blood of target user 40. Typically, a predetermined user specific (calibrated) algorithm is used by processor $\mu P_1$-28 to determine the concentration of a particular analyte. Gaskets 39 disposed between measurement subsystem 18 and wearable device 16 adjust and calibrate the distance between measurement subsystem 18 and wearable device 16 and minimize the amount of extraneous outside (contaminating) light. The measured concentration of analyte is then sent as physiological data to the vehicle control subsystem 22 as discussed above. Processor $\mu P_3$-94 then compares the measured concentration of the analyte to a predetermined threshold, or limit. If the analyte concentration, e.g. alcohol concentration is equal to or greater than the predefined limit, e.g., 0.08% blood alcohol, processor $\mu P_3$-94 initiates vehicle responses 76, as discussed above. Further details regarding the design and operation of measurement subsystem 18 and infrared spectrometer 26 are disclosed in U.S. Pat. Nos. 7,016,713, 7,271,912, 7,147,153, and U.S. Patent Application No. 2006/0173256, all of which are incorporated in their entirety by reference herein. Additional details on infrared spectrometer 26 are also disclosed in the article "Lasers Alight on a Growing Market—Maxion's quantum cascade lasers enter the market for chemical sensing and noninvasive diagnostics", by Joan Zimmerman, MDA TechUpdate, Fall 2007, incorporated by reference herein. In one example, display 110, FIG. 2A on measurement subsystem 18 displays the measured concentration percentage of the analyte in the blood of target user 12 and/or a physiological alert condition.

The result is system 10 unobtrusively and accurately measures the concentration of at least one analyte in the blood of the target user which may include the blood alcohol level of the level of the target user or the level of one or more drugs in the blood of the target user while the target user is operating the vehicle. System 10 also can unobtrusively and accurately measures the level of one or more analytes related to health conditions that may prevent the ability of the target user to safely operate the vehicle while the target user is operating the vehicle. System 10 also safely increases the driving privileges of persons commonly issued medical conditional licenses, or who are restricted from operating motor vehicles. System 10 requires no cooperation from the target user to test the level of one or more analytes in the blood of the target user. Thus, the user need not reach over and grab a breathalyzer which is cumbersome and dangerous while operating. Therefore, system 10 is less dangerous. Moreover, because the wearable device is unique matched to the measurement subsystem and affixed to target user 12 as a tamper proof device, system 10 cannot be subverted. Because system 10 preferably utilizes a measurement subsystem configured as an infrared spectrometer to accurately measure the level of one or more analytes in the blood of target user, system 10 is more accurate and eliminates false positive tests. Additionally, system 10 targets the DWI offender, not other users of the vehicle. Because system 10 is only activated when the wearable device is detected in the driver's area of the vehicle and a determination is made that the wearable device uniquely matches the measurement subsystem, those who are not convicted of DWI offenses who operate the vehicle, are unaffected by system 10. System 10 is also less expensive than conventional breathalyzer-based systems because it has lower maintenance, monitoring costs, and reduces the cost to communities of traditional detection programs, e.g., police road blocks and the like. System 10 also helps prevent habitual DWI offenses.

Figure 5:
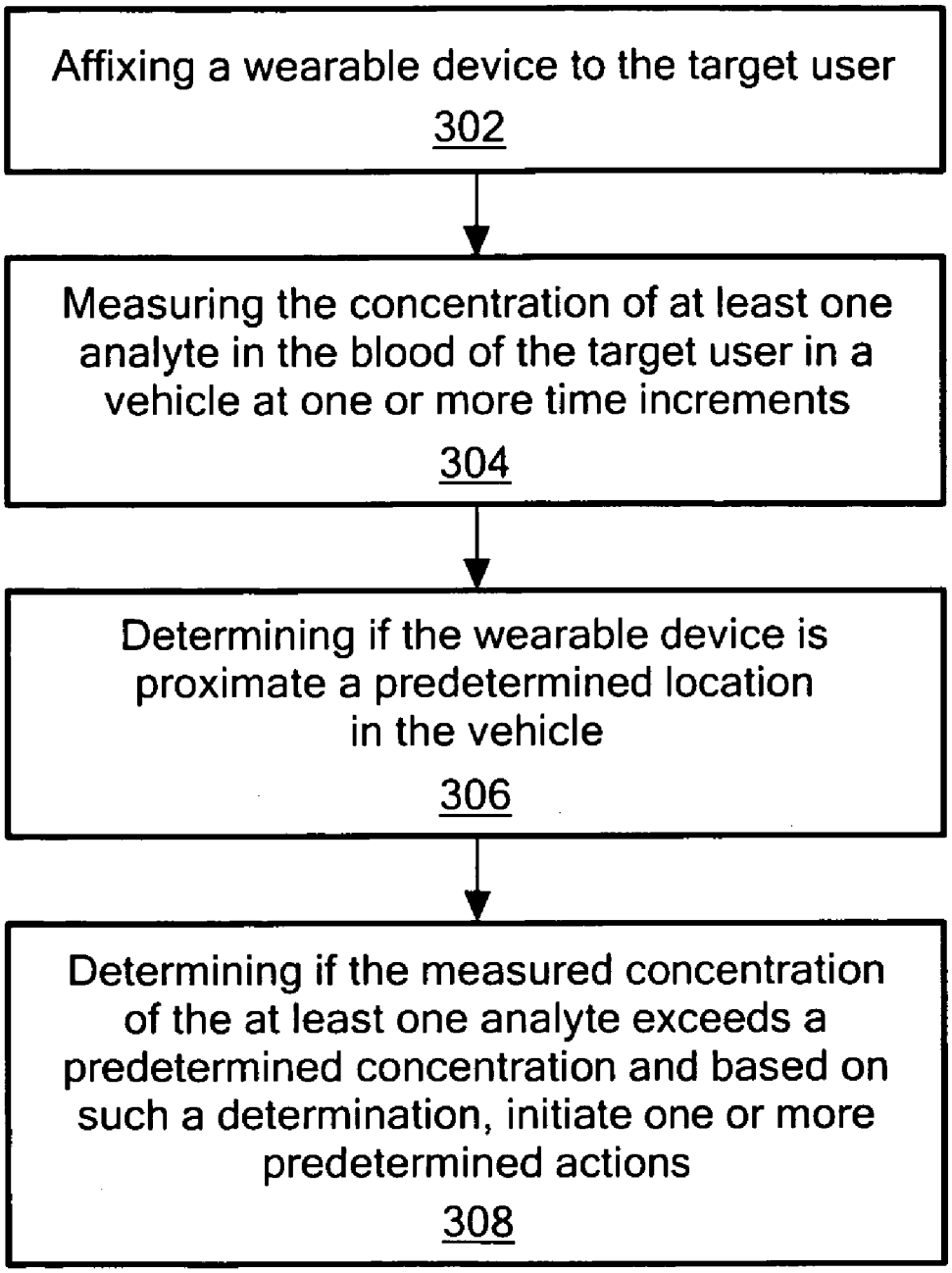
FIG. 5 is a schematic block diagram showing one embodiment of the primary steps of the unobtrusive method for monitoring the physiological condition of a target user of a vehicle.
Figure 6:
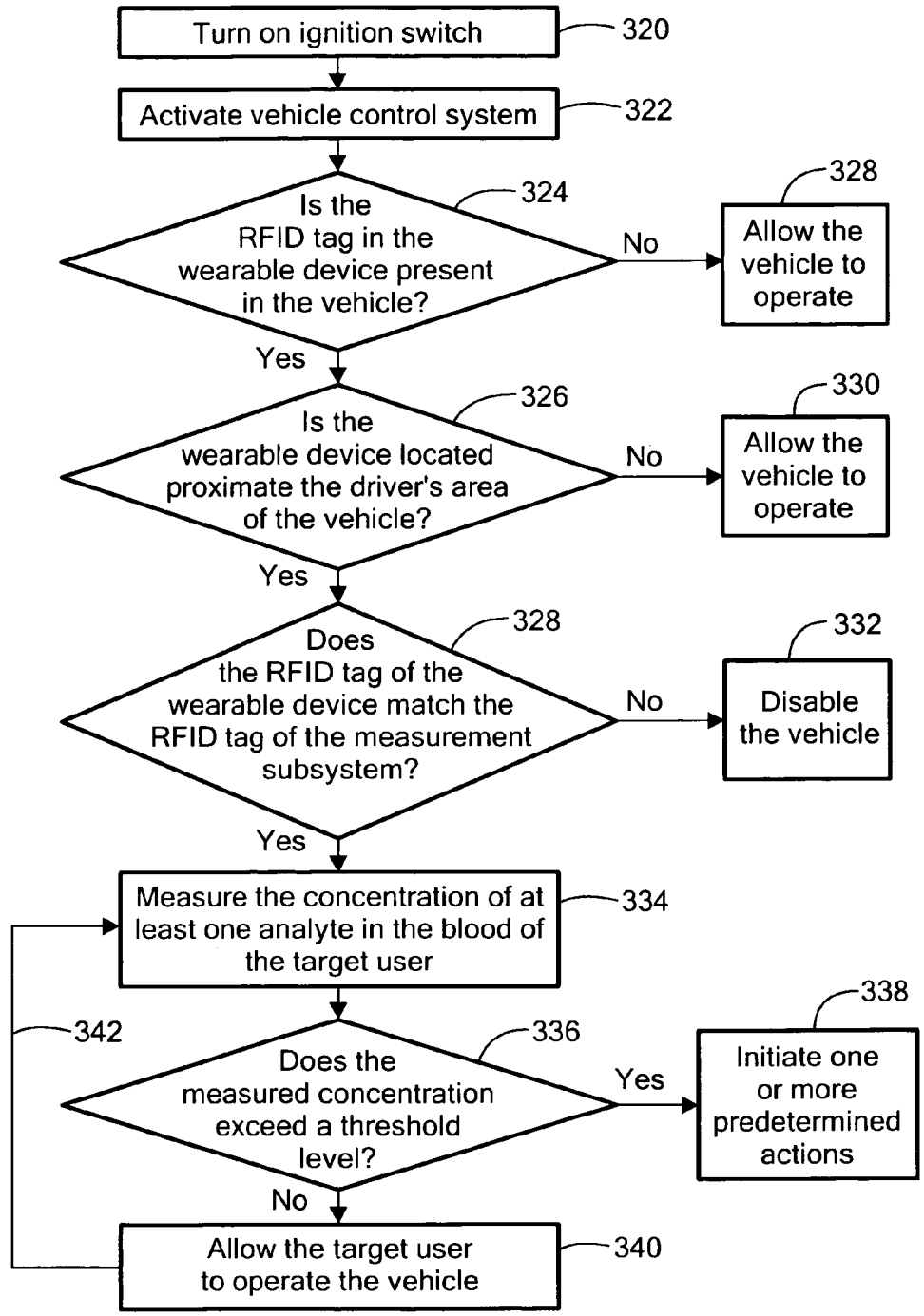
FIG. 6 is a schematic block diagram showing in further detail one example of the steps for the unobtrusive method for monitoring the physiological condition of a target user of a vehicle shown in FIG. 5.

The unobtrusive method for monitoring the physical condition of a target user includes the steps of affixing a wearable device to the target user, step 302, FIG. 5; measuring the concentration of at least one analyte in the blood of a target user at one or more time increments, step 304; determining if the wearable device is proximate a predetermined location in the vehicle, step 306; and determining if the measured concentration of the at least one analyte exceeds a predetermined threshold concentration level and based on such a determination initiate one or more predetermined actions, step 308.

In one design, the method further includes the step of emitting light at a predetermined wavelength into the subcutaneous layer of the skin of a target user and detecting the wavelength of the light emitting from the subcutaneous layer of the skin of the target user. The method may further include the step of determining a change in the wavelength of the light emitting into the subcutaneous layer of the skin of the target user and the light emitted out of the subcutaneous layer of the skin of the target user to determine the concentration of the at least one analyte in the blood of the target user. In one embodiment, the method may further include the step of determining if the wearable device is uniquely matched to the measurement subsystem.

One exemplary operation of unobtrusive system 10 and method for monitoring the physiological condition of a target user of a vehicle of this invention is described below with reference to FIGS. 1-4.

Target user 12 first engages the ignition switch of vehicle 14, step 320. This activates vehicle control subsystem 22, step 322. Vehicle location subsystem 22 then determines if RF ID tag 82 in wearable device 16 is present in vehicle 14, step 324. If RF ID tag 82 is not detected, vehicle 14 is allowed to operate, step 328. If RF ID tag 82 in wearable device 16 is located in vehicle 14, vehicle control subsystem 22, using proximity sensor 20, determines if wearable device 16 is proximate to driver's area 54 of vehicle 14, step 326. If no such determination is made, the operator is allowed to operate vehicle 14, step 330. Vehicle control subsystem 22 then determines if RF ID tag 82 in wearable device 16 uniquely matches RF ID tag 80 in measurement subsystem 18, step 328. If RF ID tag 80 in measurement subsystem 18 does not uniquely match RF ID tag 82 in wearable device 16, the vehicle is disabled, step 332. If RF ID tag 82 in wearable device 16 uniquely matches RF ID tag 80 in measurement subsystem 18, vehicle control subsystem initiates measurement subsystem 18 to measure the concentration of at least one analyte in the blood of target user 12, step 334. Vehicle control subsystem 22 then determines whether the measured concentration of the at least one analyte in the blood of the target user exceeds a threshold level, step 336. If such a condition exists, vehicle control subsystem 22 initiates one or more predetermined actions, step 338. If the measured concentration of the at least one analyte does not exceed a threshold level, the operator is allowed to drive the vehicle, step 340. Thereafter, at various time increments, vehicle control subsystem 22 activates measurement subsystem 18 to measure the concentration of at least one analyte in the blood of the target user, step 342. Steps 334 and 336 are repeated at various times while the target user is operating the vehicle.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. An unobtrusive system for monitoring the physiological condition of a target user of a vehicle comprising:
a wearable device affixed to the target user;
a measurement subsystem releasably coupled to the wearable device configured to measure a concentration of at least one analyte in the blood of the target user at one or more time increments; wherein at least one analyte includes an analyte chosen from the group consisting of: alcohol, drugs, glucose, proteins, enzymes, hormones, glucose ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, narcotics, tetrahydrocannabinol, cytochrome, various proteins and chromophores, microcalcifications, electrolytes, sodium, potassium, chloride, bicarbonate, and hormones;

a proximity sensor configured to detect the location of the wearable device; and a vehicle control subsystem responsive to the proximity sensor and the measurement subsystem configured to determine if the wearable device is proximate a predetermined location in the vehicle and configured to determine if the measured concentration of the at least one analyte exceeds a predetermined threshold concentration level, and based on such a determination, initiate one or more predetermined actions.

2. The system of claim 1 in which the measurement subsystem is configured as an infrared spectrometer.

3. The system of claim 2 in which the infrared spectrometer includes one or more processors and a power supply located in the measurement subsystem and one or more processors, a light source, and a photodetector located in the wearable device.

4. The system of claim 3 in which the light source emits light at a predetermined wavelength into the subcutaneous layer of the skin of the target user and the photodetector detects the wavelength of the reflected light emitted the subcutaneous layer of the skin of the target user.

5. The system of claim 4 in which the measurement subsystem determines a change in the wavelength of the light emitted by the light source and the light detected by the photodetector to determine the concentration of the at least one analyte in the blood of the target user.

6. The system of claim 3 in which the measurement subsystem includes one or more contacts for connecting to a power source for recharging the power supply.

7. The system of claim 3 further including one or more gaskets disposed between the measurement subsystem and the wearable device configured to adjust the distance between the measurement subsystem and the wearable device and minimize extraneous light.

8. The system of claim 1 in which the measurement subsystem is uniquely matched to the wearable device.

9. The system of claim 8 in which the measurement subsystem includes a unique RF ID tag.

10. The system of claim 9 in which the wearable device includes a unique RF ID tag.

11. The system of claim 10 in which the measurement subsystem is configured to transmit physiological data of the measured concentration of the at least one analyte in the blood of the target user to the vehicle control subsystem when the RF ID tag of the measurement subsystem uniquely matches the RF ID tag of the wearable device.

12. The system of claim 10 in which the wearable device includes a processor configured to determine the identity of the RF ID tag of the wearable device.

13. The system of claim 12 in which the measurement subsystem includes a processor configured to determine if the identity of RF ID tag located in the measurement subsystem and if the RF ID tag of the measurement subsystem uniquely matches the RF ID tag of the wearable device.

14. The system of claim 12 in which the wearable device includes one or more processors and one or more transmitters.

15. The system of claim 12 in which the vehicle control subsystem includes one or more processors, one or more transmitters and one or more receivers.

16. The system of claim 15 further including a power supply coupled to the vehicle control system.

17. The system of claim 1 in which the wearable device includes a tamper proof bracket.

18. The system of claim 1 in which the wearable device includes a tamper proof anklet.

19. The system of claim 1 in which the wearable deice is coupled to the measurement subsystem by one or more electrical contacts.

20. The system of claim 1 in which the proximity sensor includes a DC pulse magnetic resonator configured to detect the distance and spatial orientation of a magnetic sensor located in the wearable device.

21. The system of claim 20 in which the proximity sensor is located in the vehicle.

22. The system of claim 20 in which the proximity sensor is located proximate the steering column of the vehicle.

23. The system of claim 20 in which the vehicle control system, responsive to signals from the proximity sensor, defines the predetermined location in the vehicle.

24. The system of claim 23 in which the vehicle control system is configured to determine if the wearable device is proximate the predetermined location in the vehicle.

25. The system of claim 24 in which the predetermined location is the area proximate the driver's area of the vehicle.

26. The system of claim 25 in which the proximity sensor communicates to the vehicle control subsystem by a direct connection.

27. The system of claim 26 in which the proximity sensor communicates to the vehicle control system wirelessly.

28. The system of claim 1 in which the one or more time increments include a first time the target user starts the vehicle and thereafter at random and/or predetermined time increments.

29. The system of claim 1 in which the predetermined threshold concentration level includes about 0.08% alcohol in the blood of the target user, and/or a measurable amount of illegal drugs in the blood of the target user and/or a change in protein-c levels in the blood of the target user that may be indicative of a heart attack in the blood of the target user and/or an unsafe blood glucose level in the blood of the target user.

30. An unobtrusive method for monitoring the physiological condition of a target user of a vehicle comprising:

affixing a wearable device to a target user;

measuring the concentration of at least one analyte in the blood of a target user in the vehicle one or more time increments; wherein at least one analyte includes an analyte chosen from the group consisting of: alcohol, drugs, glucose, proteins, enzymes, hormones, glucose ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, narcotics, tetrahydrocannabinol, cytochrome, various proteins and chromophores, microcalcifications, electrolytes, sodium, potassium, chloride, bicarbonate, and hormones;

determining if the wearable device is proximate a predetermined location in the vehicle; and determining if the measured concentration of at least one analyte exceeds a predetermined threshold concentration level and based on such a determination, initiate one or more predetermined actions.

31. The method of claim 30 further including the step of emitting light at a predetermined wavelength into the subcutaneous layer of the skin of a target user and detecting the wavelength of the light emitted from the subcutaneous layer of the skin of the target user.

32. The method of claim 31 further including the step of determining a change in the wavelength of the light emitted into the subcutaneous layer of the skin of the target user, and the light emitted out of the subcutaneous layer of the skin of the target user to determine the concentration of the at least one analyte in the blood of the target user.

33. The method of claim 30 further including the step of determining if the wearable device is uniquely matched to the measurement subsystem.

34. The method of claim 30 in which the predetermined threshold concentration level includes about 0.08% alcohol in the blood of the target user and/or a measurable amount of illegal drugs in the blood of the target user and/or a change in protein-c levels that may be indicative of a heart attack in the blood of the target user and/or an unsafe blood glucose level in the blood of the target user.

* * * * *